(12) United States Patent
Chen et al.

(10) Patent No.: US 11,040,195 B2
(45) Date of Patent: Jun. 22, 2021

(54) SYSTEMS AND METHODS FOR REDUCING RF HEATING IN IMPLANTABLE LEADS

(71) Applicant: PACESETTER, INC., Sylmar, CA (US)

(72) Inventors: Xi Lin Chen, Valencia, CA (US); Shiloh Sison, Alameda, CA (US)

(73) Assignee: PACESETTER, INC., Sylmar, CA (US)

( * ) Notice: Subject to any disclaimer, the term of this patent is extended or adjusted under 35 U.S.C. 154(b) by 103 days.

(21) Appl. No.: 16/194,136

(22) Filed: Nov. 16, 2018

(65) Prior Publication Data

US 2020/0155836 A1 May 21, 2020

(51) Int. Cl.

| A61N 1/37 | (2006.01) |
|---|---|
| A61N 1/08 | (2006.01) |
| A61N 1/378 | (2006.01) |
| A61N 1/05 | (2006.01) |
| A61N 1/375 | (2006.01) |
| A61N 1/36 | (2006.01) |

(52) U.S. Cl.
CPC ........... *A61N 1/086* (2017.08); *A61N 1/3718* (2013.01); *A61N 1/0551* (2013.01); *A61N 1/36125* (2013.01); *A61N 1/3706* (2013.01); *A61N 1/3754* (2013.01); *A61N 1/3787* (2013.01); *A61N 1/37512* (2017.08)

(58) Field of Classification Search
CPC .... A61N 1/086; A61N 1/3718; A61N 1/3706; A61N 1/3787; A61N 1/3754; A61N 1/0551; A61N 1/36125; A61N 1/37512
See application file for complete search history.

(56) References Cited

U.S. PATENT DOCUMENTS

| 2006/0247747 A1* | 11/2006 | Olsen ................. A61N 1/36142 607/116 |
| 2008/0221568 A1* | 9/2008 | Stone ....................... A61N 1/05 606/42 |
| 2011/0172756 A1* | 7/2011 | Doerr ....................... A61N 1/05 623/1.15 |

* cited by examiner

*Primary Examiner* — Rex R Holmes
(74) *Attorney, Agent, or Firm* — The Small Patent Law Group LLC; Dean D. Small

(57) ABSTRACT

The present disclosure provides systems and methods for reducing RF heating in implantable leads. An implantable lead includes a first electrode, and a coupling component spaced from the first electrode, wherein the first electrode and the coupling component form a capacitor, wherein the first electrode and the coupling component are electrically isolated from one another at therapy frequencies, and wherein the first electrode and the coupling component are electrically coupled to one another at magnetic resonance imaging (MRI) frequencies.

14 Claims, 9 Drawing Sheets

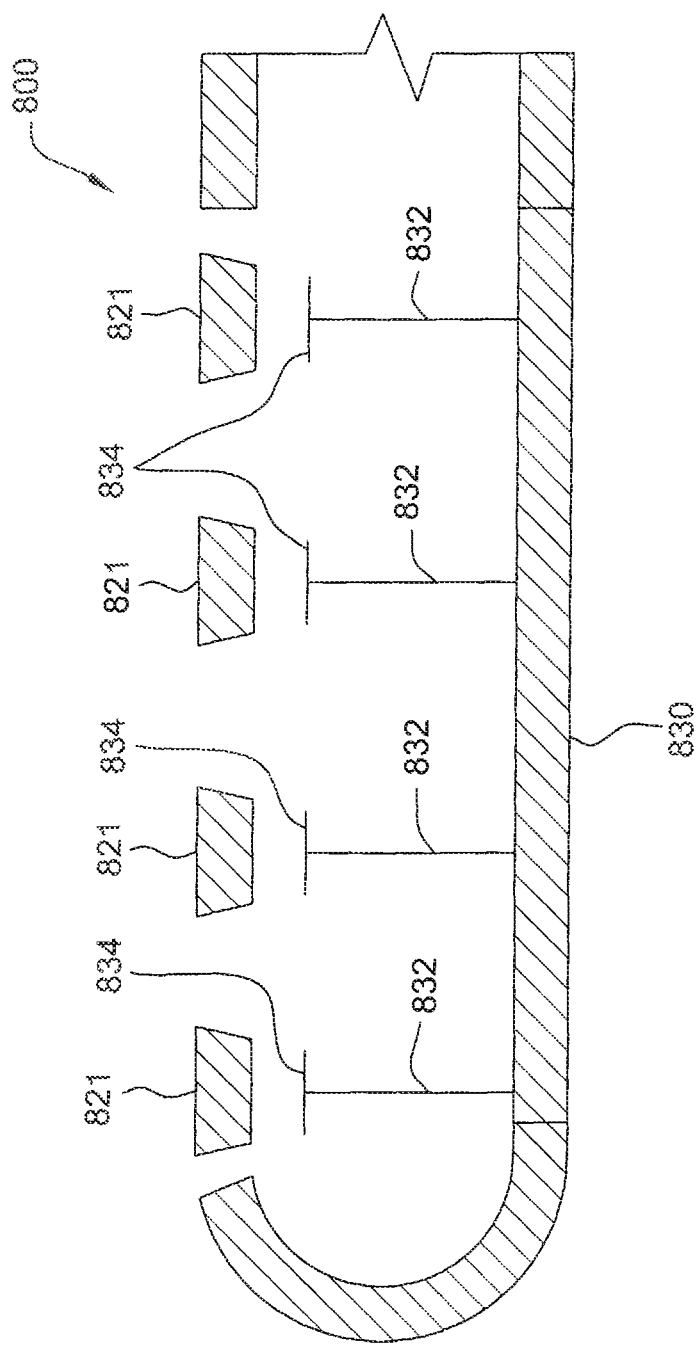

SYSTEMS AND METHODS FOR REDUCING RF HEATING IN IMPLANTABLE LEADS

A. FIELD OF THE DISCLOSURE

The present disclosure relates generally to implantable medical devices, and more particularly to reducing radio frequency (RF) heating in implantable leads during magnetic resonance imaging (MRI) therapy.

B. BACKGROUND ART

Implantable medical devices, such as cardiac stimulation devices and neurostimulation devices typically include one or more implantable leads. When a patient having an implantable medical device undergoes Magnetic Resonance Imaging (MRI) therapy, the radio frequency (RF) field generated during the MRI therapy can induce current on an implanted lead. This induced current may trigger power deposition on electrodes on the implanted lead, which causes RF heating of tissue surrounding the electrode.

To attempt to reduce the RF heating effect of an electrode, at least some known implanted leads have an enlarged surface area to reduce RF power density. However, the enlarged surface area effects the operation of the electrodes at therapeutic frequencies (i.e., pacing or stimulation frequencies that are typically much lower than MRI frequencies). For example, for a cardiac pacing lead, a larger electrode surface can impact a pacing capture threshold. At least some other known implanted leads use a dummy electrode connected to lead conductors via an RF filter, adding complexity and components to the implanted lead. Accordingly, it would be desirable to provide a simple and effective way of reducing RF heating of implanted lead electrodes, without impacting operation of the implanted lead electrodes at therapeutic frequencies.

BRIEF SUMMARY OF THE DISCLOSURE

In one embodiment, the present disclosure is directed to an implantable lead. The implantable lead includes a first electrode, and a coupling component spaced from the first electrode, wherein the first electrode and the coupling component form a capacitor, wherein the first electrode and the coupling component are electrically isolated from one another at therapy frequencies, and wherein the first electrode and the coupling component are electrically coupled to one another at magnetic resonance imaging (MRI) frequencies.

In another embodiment, the present disclosure is directed to an implantable medical device. The implantable medical device includes an implantable pulse generator (IPG), and an implantable lead coupled to the IPG. The implantable lead includes a first electrode, and a coupling component spaced from the first electrode, wherein the first electrode and the coupling component form a capacitor, wherein the first electrode and the coupling component are electrically isolated from one another at therapy frequencies, and wherein the first electrode and the coupling component are electrically coupled to one another at magnetic resonance imaging (MRI) frequencies.

In yet another embodiment, the present disclosure is directed to a method of assembling an implantable lead. The method includes positioning a coupling component in a spaced relationship with a first electrode of the implantable lead, wherein the first electrode and the coupling component form a capacitor, wherein the first electrode and the coupling component are electrically isolated from one another at therapy frequencies, and wherein the first electrode and the coupling component are electrically coupled to one another at magnetic resonance imaging (MRI) frequencies.

The foregoing and other aspects, features, details, utilities and advantages of the present disclosure will be apparent from reading the following description and claims, and from reviewing the accompanying drawings.

BRIEF DESCRIPTION OF THE DRAWINGS

FIG. 9 is a cross-sectional schematic view of the SCS lead shown in FIG. 8 and a coupling component.

Corresponding reference characters indicate corresponding parts throughout the several views of the drawings.

DETAILED DESCRIPTION OF THE DISCLOSURE

The present disclosure provides systems and methods for reducing RF heating in implantable leads. An implantable lead includes a first electrode, and a coupling component spaced from the first electrode. The first electrode and the coupling component form a capacitor. The first electrode and the coupling component are electrically isolated from one another at therapy frequencies, but are electrically coupled to one another at magnetic resonance imaging (MRI) frequencies. The combined surface area of the first electrode and the coupling component facilitates dissipating radio frequency (RF) energy at MRI frequencies.

Figure 1:
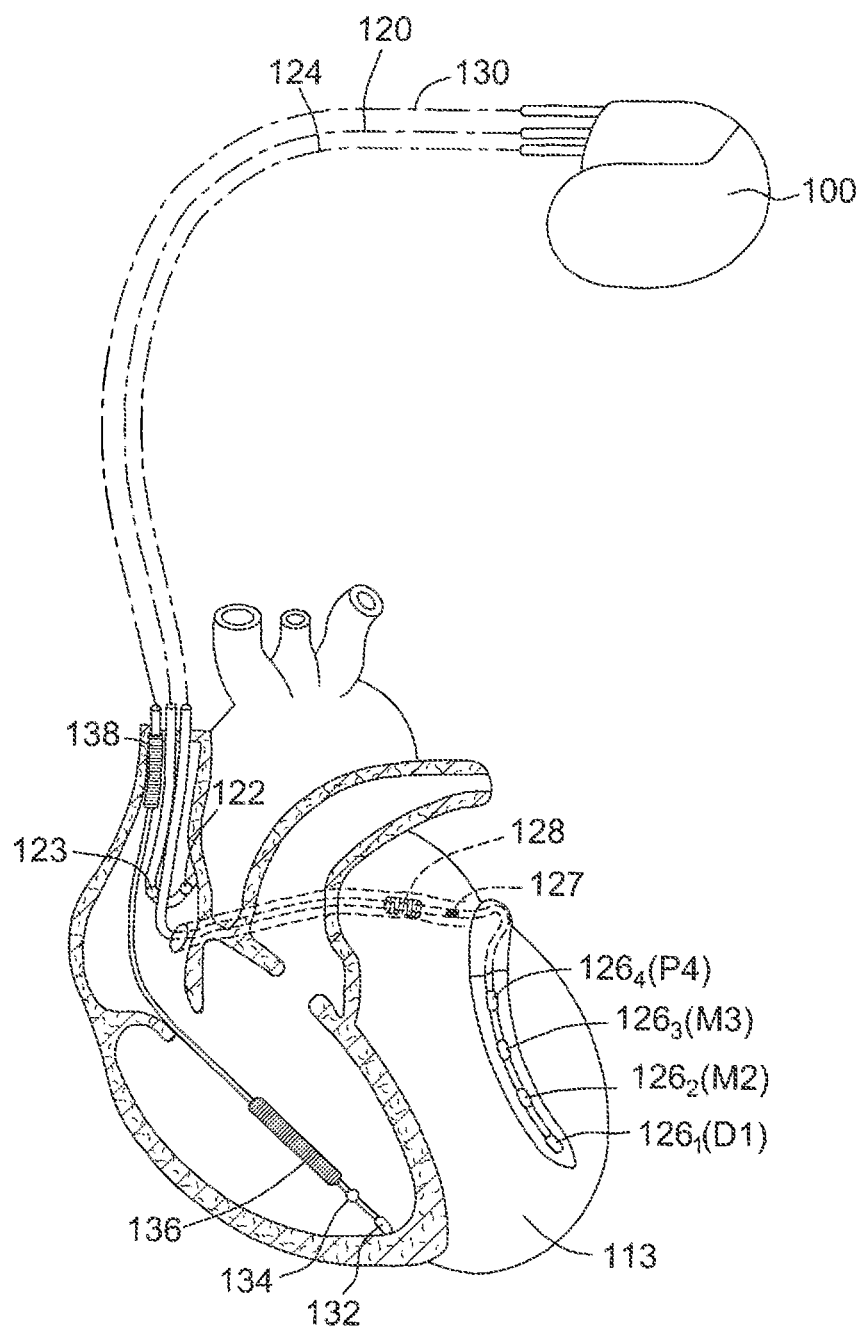
FIG. 1 is a simplified, partly cutaway view illustrating an implantable stimulation device in electrical communication with at least three leads implanted into a patient's heart for delivering multi-chamber stimulation and shock therapy and sensing cardiac activity.

Referring now to the drawings, FIG. 1 is a simplified block diagram of a pacemaker/ICD 100, which is a dual-chamber stimulation device capable of treating both fast and slow arrhythmias with stimulation therapy, including cardioversion, defibrillation, and pacing stimulation, including multipoint pacing (MPP). To provide atrial chamber pacing stimulation and sensing, pacemaker/ICD 100 is shown in electrical communication with a heart 113 by way of a right atrial (RA) lead 120 having an atrial tip electrode 122 and an atrial ring electrode 123 implanted in the atrial appendage. Pacemaker/ICD 100 is also in electrical communication with heart 113 by way of a right ventricular (RV) lead 130 having, in this embodiment, a ventricular tip electrode 132, a RV ring electrode 134, a RV coil electrode 136, and a superior vena cava (SVC) coil electrode 138. Typically, RV lead 130 is transvenously inserted into the heart so as to place RV coil electrode 136 in the RV apex, and SVC coil electrode 138 in the superior vena cava. Accordingly, RV lead 130 is capable of receiving cardiac signals, and delivering stimulation in the form of pacing and shock therapy to the right ventricle (also referred to as the RV chamber).

To sense left atrial and ventricular cardiac signals and to provide left chamber pacing therapy, pacemaker/ICD 100 is coupled to a multi-pole left ventricular (LV) lead 124 designed for placement in the "CS region" for positioning a distal electrode adjacent to the left ventricle and/or additional electrode(s) adjacent to the left atrium (also referred to as the LA chamber). As used herein, the phrase "CS region" refers to the venous vasculature of the left ventricle, including any portion of the coronary sinus (CS), great cardiac vein, left marginal vein, left posterior ventricular vein, middle cardiac vein, small cardiac vein, and/or any other cardiac vein accessible by the CS. Accordingly, an example LV lead 124 is designed to receive atrial and ventricular cardiac signals and to deliver left ventricular pacing therapy using a set of four LV electrodes $126_1$, $126_2$, $126_3$, and $126_4$ (thereby providing a quadra-pole lead), left atrial pacing therapy using at least a LA ring electrode 127, and shocking therapy using at least a LA coil electrode 128. In some embodiments, LV lead 124 includes LV electrodes $126_1$, $126_2$, $126_3$, and $126_4$, but does not include LA ring and coil electrodes 127 and 128. Such a lead can be, e.g., the Quartet™ left ventricular pacing lead developed by Abbott Laboratories, which includes four pacing electrodes on the left ventricular lead—enabling up to ten pacing configurations LV electrode $126_1$ is shown as being the most "distal" LV electrode (with relation to how far the electrode is from where LV lead 124 connects to pacemaker/ICD 100). For example LV electrode $126_1$ may be located at the apex of the left ventricle. LV electrode $126_4$ is shown as being the most "proximal" LV electrode. For example LV electrode $126_4$ may be located at the base of the left ventricle. LV electrodes $126_2$ and $126_3$ are shown as being "middle" LV electrodes, between distal and proximal LV electrodes $126_1$ and $126_4$. Accordingly, the four LV electrodes $126_1$, $126_2$, $126_3$, and $126_4$ can be referred to respectively as electrodes D1, M2, M3 and P4 (where "D" stands for "distal", "M" stands for "middle", and "P" stands from "proximal", and the numbers are arranged from most distal to most proximal). It is also possible that more or fewer LV electrodes are provided.

Figure 2:
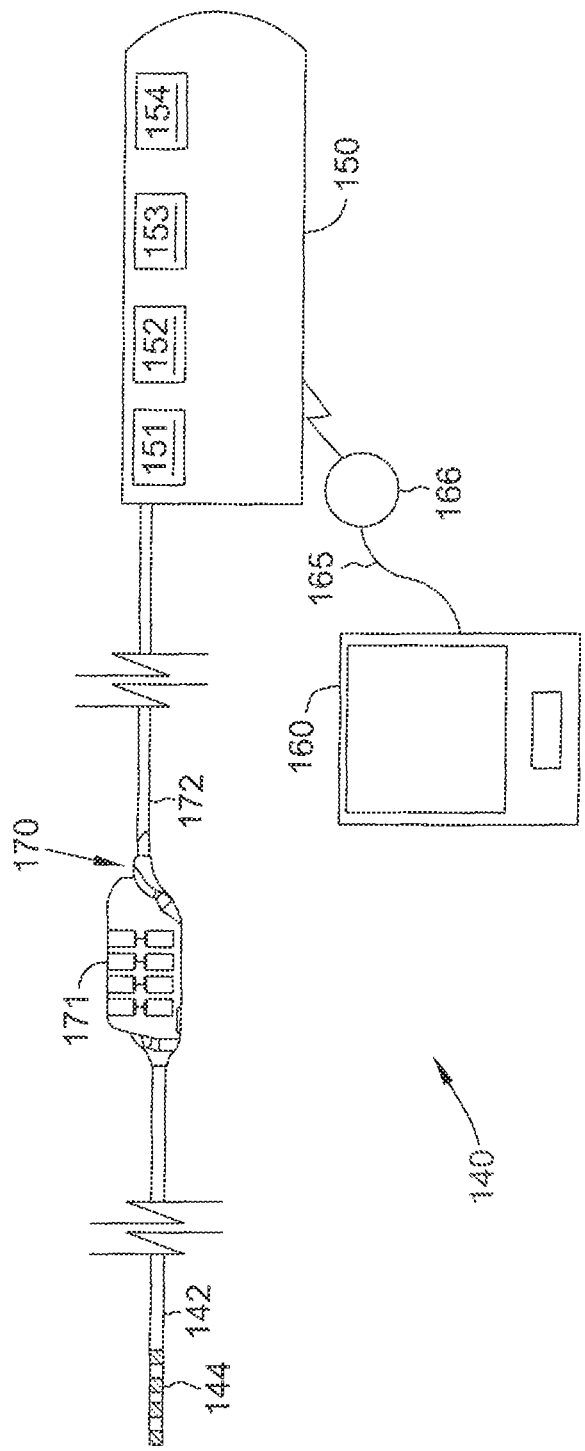
FIG. 2 is a schematic view of one embodiment of a neurostimulation system.

FIG. 2 is a schematic view of one embodiment of a stimulation system 140. Stimulation system 140 generates electrical pulses for application to tissue of a patient, or subject, according to one embodiment. System 140 includes an implantable pulse generator (IPG) 150 that is adapted to generate electrical pulses for application to tissue of a patient. Alternatively, system 140 may include an external pulse generator (EPG) positioned outside the patient's body. IPG 150 typically includes a metallic housing that encloses a controller 151, pulse generating circuitry 152, a battery 153, far-field and/or near field communication circuitry 154, and other appropriate circuitry and components of the device. Controller 151 typically includes a microcontroller or other suitable processor for controlling the various other components of the device. Software code is typically stored in memory of IPG 150 for execution by the microcontroller or processor to control the various components of the device.

IPG 150 may comprise one or more attached extension components 170 or be connected to one or more separate extension components 170. Alternatively, one or more stimulation leads 142 may be connected directly to IPG 150. Within IPG 150, electrical pulses are generated by pulse generating circuitry 152 and are provided to switching circuitry. The switching circuit connects to output wires, traces, lines, or the like (not shown) which are, in turn, electrically coupled to internal conductive wires (not shown) of a lead body 172 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from IPG 150 and conducted through the conductors of lead body 172 are provided to stimulation lead 142. The pulses are then conducted through the conductors of lead 142 and applied to tissue of a patient via electrodes 144. Any suitable known or later developed design may be employed for connector portion 171.

Stimulation lead(s) 142 may include a lead body of insulative material about a plurality of conductors within the material that extend from a proximal end of lead 142 to its distal end. The conductors electrically couple a plurality of electrodes 144 to a plurality of terminals (not shown) of lead 142. The terminals are adapted to receive electrical pulses and the electrodes 144 are adapted to apply stimulation pulses to tissue of the patient. Also, sensing of physiological signals may occur through electrodes 144, the conductors, and the terminals. Additionally or alternatively, various sensors (not shown) may be located near the distal end of stimulation lead 142 and electrically coupled to terminals through conductors within the lead body 172. Stimulation lead 142 may include any suitable number and type of electrodes 144, terminals, and internal conductors.

A controller device 160 may be implemented to recharge battery 153 of IPG 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller device 160 generates an AC-signal to drive current through coil 166 of wand 165. Assuming that primary coil 166 and secondary coil are suitably positioned relative to each other, the secondary coil is disposed within the field generated by the current driven through primary coil 166. Current is then induced in secondary coil. The current induced in the coil of the implantable pulse generator is rectified and regulated to recharge battery of IPG 150. The charging circuitry may also communicate status messages to controller device 160 during charging operations using pulse-loading or any other suitable technique. For example, controller device 160 may communicate the coupling status, charging status, charge completion status, etc.

The systems and methods described herein facilitate reducing RF heating of an implantable lead body during MRI therapy. Specifically, the systems and methods described herein reduce heating by having a relatively large electrode surface at MRI frequencies while having a smaller electrode surface during pacing or stimulation therapy. The heating reduction is achieved by electrically coupling a first electrode (e.g., a tip electrode) and a second electrode (e.g., a ring electrode) at MRI frequencies using a coupling component such that power deposited on the first electrode is distributed to the second electrode. The combination of the first and second electrodes has a larger surface area than the first electrode alone. Further, at pacing or stimulation frequencies, the first and second electrodes are electrically decoupled from one another.

Figure 3:
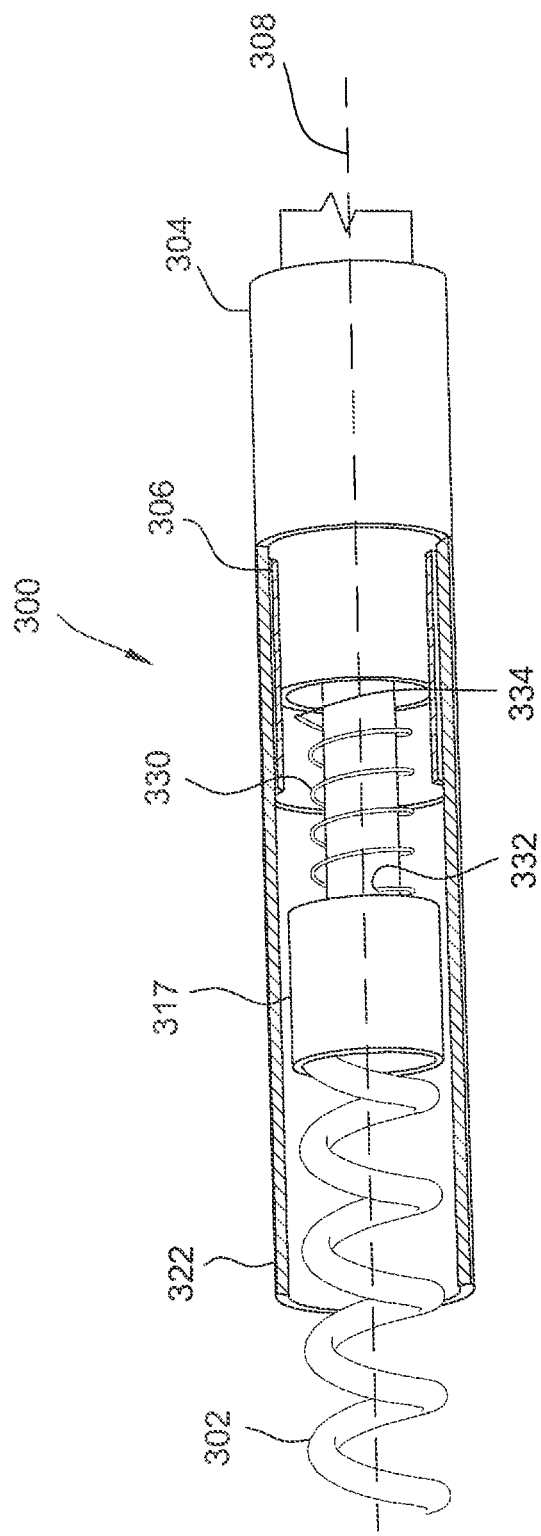
FIG. 3 is a partial cross-sectional perspective view of a portion of one embodiment of an implantable lead for reducing RF heating during MRI therapy.
Figure 4:
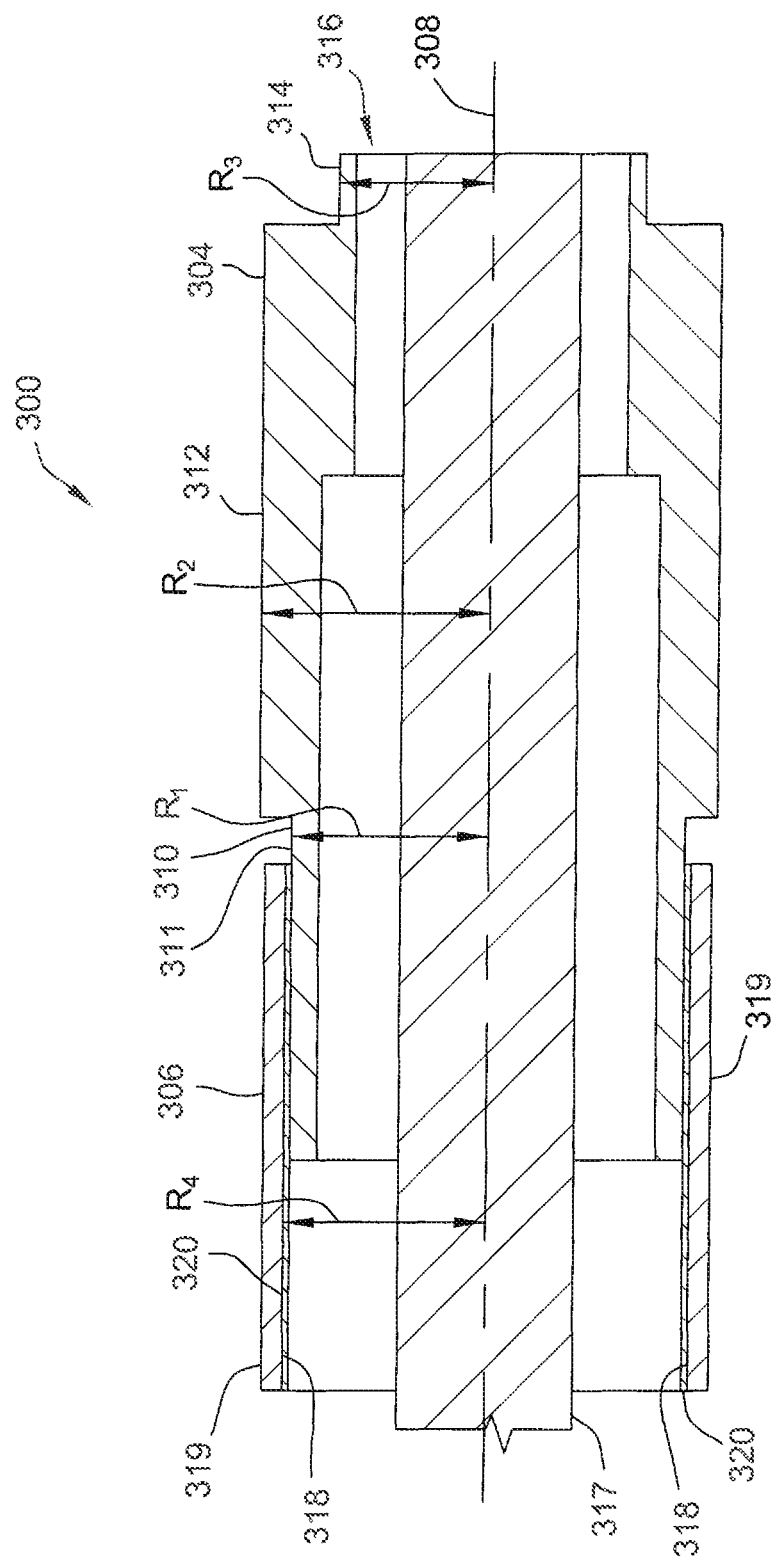
FIG. 4 is a cross-sectional view of a ring coupler and a ring electrode that may be used with the implantable lead shown in FIG. 3.

FIG. 3 is a partial cross-sectional perspective view of a portion of one embodiment of an implantable lead 300 for reducing RF heating during MRI therapy. Lead 300 includes a helical tip electrode 302, a ring electrode 304, and a ring coupler 306. Ring coupler 306 may be referred to generally as a coupling component. Ring coupler 306 is located adjacent ring electrode 304 in this embodiment. FIG. 4 is a cross-sectional view of ring coupler 306 and ring electrode 304.

As shown in FIGS. 3 and 4, ring electrode 304 includes three segments that are generally annular about a longitudinal axis 308 of lead 300. Specifically, in this embodiment, ring electrode 304 includes a distal annular segment 310, a proximal annular segment 314, and an intermediate annular segment 312 extending between the distal and proximal annular segments 310 and 314. Further, annular segments 310, 312, and 314 define a cavity 316 therein. A conductor 317 electrically coupled to tip electrode 302 and capable of applying a voltage to tip electrode 302 (i.e., for stimulation) extends through cavity 316 along longitudinal axis 308.

Distal annular segment 310 defines a first radius, $R_1$, to an outer surface 311 of distal annular segment 310. Similarly, intermediate annular segment 312 defines a second radius, $R_2$, and proximal annular segment 314 defines a third radius, $R_3$. In this embodiment, $R_2 > R_1 > R_3$. Alternatively, annular segments 310, 312, and 314 may have any radii that enable ring electrode 304 to function as described herein.

In this embodiment, ring coupler 306 is a thin-walled annular tube including an inner surface 318 and an outer surface 319. Ring coupler 306 is a conductive material and may be, for example, Pt/Ir 90/10 (which may also be used for ring electrode 304). Further, ring coupler 306 defines a fourth radius, R4, from longitudinal axis 308 to inner surface 318. As shown in FIGS. 3 and 4, the fourth radius R4 is greater than the first radius $R_1$ such that at least a portion of ring coupler 306 surrounds distal annular segment 310. Ring coupler 306 does not physically contact distal annular segment 310 or any other portion of ring electrode 304. Instead, a dielectric layer 320 is positioned between and extends between ring coupler 306 and distal annular segment 310. That is, dielectric layer 320 contacts inner surface 318 of ring coupler 306 and outer surface 311 of distal annular segment 310.

Dielectric layer 320 is a non-conductive dielectric material having a high dielectric strength and capable of withstanding high voltages (e.g., from an external defibrillator shock). The dielectric material may have, for example, a relative permittivity value of approximately 300. Further the dielectric material may be, for example, a ceramic dielectric material such as titanium dioxide or barium titanate. In some embodiments, dielectric layer 320 includes multiple layers. Alternatively, dielectric material may have any properties that enable dielectric layer 320 to function as described herein.

Accordingly, in this embodiment, a ring capacitor structure is formed by ring coupler 306, distal annular segment 310, and dielectric layer 320. In this embodiment, ring coupler 306 is covered by a tubular insulation material 322 (shown in FIG. 3 and omitted in FIG. 4 for clarity). Accordingly, ring coupler 306 is not exposed to tissue when lead 300 is implanted.

At relatively low frequencies (e.g., at frequencies for performing stimulation and/or sensing using lead 300, referred to herein as therapeutic frequencies), ring coupler 306 and ring electrode 304 are electrically isolated from one another. However, at relatively high frequencies (e.g., MRI frequencies), the capacitance between ring coupler 306 and ring electrode 304 causes ring coupler 306 to electrically couple to ring electrode 304. Further, dielectric layer 320 increases the capacitance. Therapeutic frequencies for lead 300 may be, for example, from approximately 1 to 3 Hz. Further, MRI frequencies may be, for example, approximately 10 MHz and above (e.g., 64 MHz or 128 MHz).

As shown in FIG. 3, in the exemplary embodiment, ring coupler 306 is electrically coupled and physically coupled to tip electrode 302 via a flexible mechanism 330. In this embodiment, flexible mechanism 330 includes a first end 332 coupled to tip electrode 302 (specifically, conductor 317) and a second end 334 coupled to ring coupler 306. Flexible mechanism 330 allows tip electrode 302 to move (e.g., rotate) relative to ring coupler 306 (e.g., when tip electrode 302 is being inserted into or removed from tissue) while keeping ring coupler 306 electrically coupled to tip electrode 302. Flexible mechanism 330 does not contact ring electrode 304. In some embodiments, flexible mechanism 330 is a spring, for example.

At relatively high frequencies (e.g., MRI frequencies), tip electrode 302 is electrically coupled to ring electrode 304 through flexible mechanism 330 and ring coupler 306. This modifies the RF heating characteristics of lead 300. Specifically, because tip electrode 302 electrically couples to ring electrode 304 at higher frequencies, the surface area over which RF energy is dissipated is larger than if tip electrode 302 were electrically isolated from ring electrode 304. This results in less overall heat being generated by lead 300.

Further, the capacitance between ring coupler 306 and ring electrode 304 does not affect stimulation or sensing signals during operation of lead 300 at lower frequencies. Table 1 shows resistance values at varying frequencies for a fixed capacitance between ring coupler 306 and ring electrode 304 of $1.12 \times 10^{-10}$ Farads (F).

TABLE 1

| Frequency | Capacitance (F) | Resistance (Ω) |
|---|---|---|
| 1.0 kHz | $1.12 \times 10^{-10}$ | $1.4 \times 10^6$ |
| 64 MHz | | 22.0 |
| 128 MHz | | 11.0 |

As shown by Table 1, the resistance between ring coupler 306 and ring electrode 304 is very high at low frequencies, but much lower at high frequencies. Thus, at low frequencies, ring coupler 306 and ring electrode 304 are effectively electrically isolated from one another.

Figure 5:
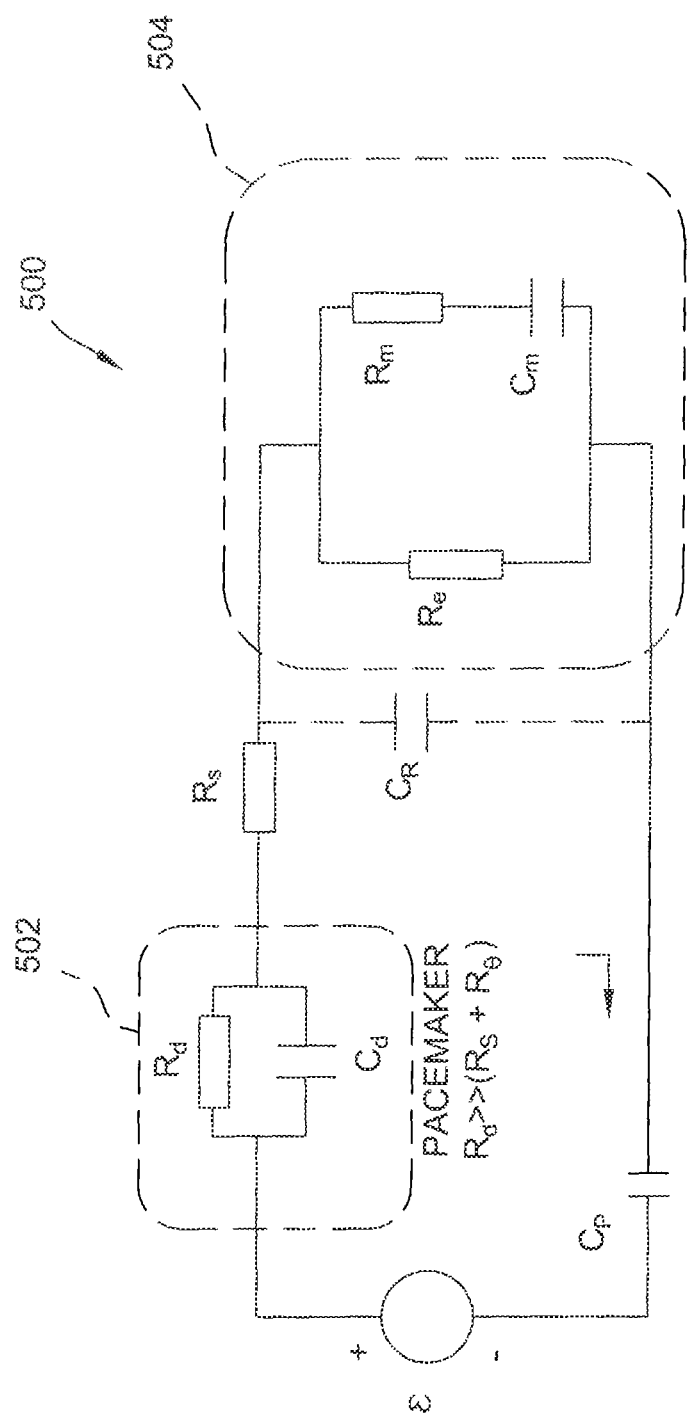
FIG. 5 is a circuit diagram of a circuit that models electrical interactions between an implantable medical device including the implantable lead shown in FIG. 3 and patient tissue.

FIG. 5 is a circuit diagram of a circuit 500 that models the electrical interactions between an implantable medical device including lead 300 (shown in FIGS. 3 and 4) and patient tissue. Specifically, in this example, the implantable medical device is a pacemaker 502, and the patient tissue is a patient heart 504. Alternatively, other implantable medical devices and patient tissue could be modeled, as will be appreciated by one of skill in the art.

In circuit 500, $R_e$ represents a bulk impedance of heart 504, the series RC ($R_m$ and $C_m$) represents an excitable cell membrane of heart 504, $R_s$ represents a resistance of lead 300, $R_d$ represents a resistance of pacemaker 502, $C_P$ represents a pace return capacitor, and $C_d$ represents a feedthrough capacitor of pacemaker 502. $C_R$ represents the capacitance between ring coupler 306 and ring electrode 304, and appears in parallel to the pacemaker voltage source, ε, after the lead resistance $R_s$ and before heart 504. Based on the value in Table 1 above, at 1 kHz, $C_R$ will have an equivalent series resistance value of 1400 kW, making it transparent to the pacing therapy. That is, $C_R$ will not change the patient load and the pacing capacitance (which is dominated by $C_P$).

As explained above, the systems and methods described herein are not limited to use with pacemakers or other cardiac devices. Instead the systems and methods described herein may be implemented in any suitable implantable device lead.

Figure 6:
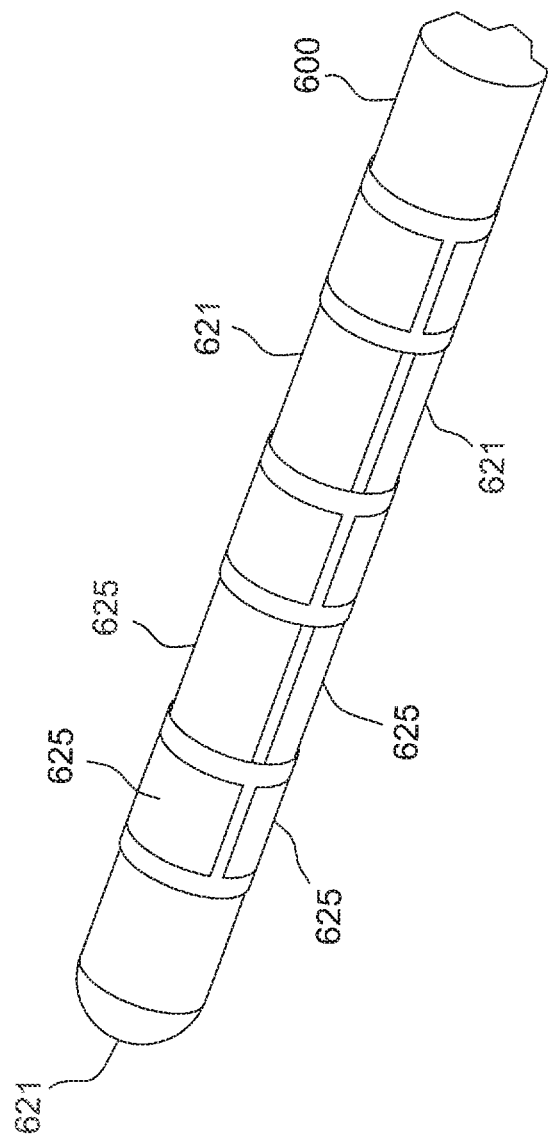
FIG. 6 is a schematic view of a portion of one embodiment of a deep brain stimulation (DBS) lead.
Figure 7:
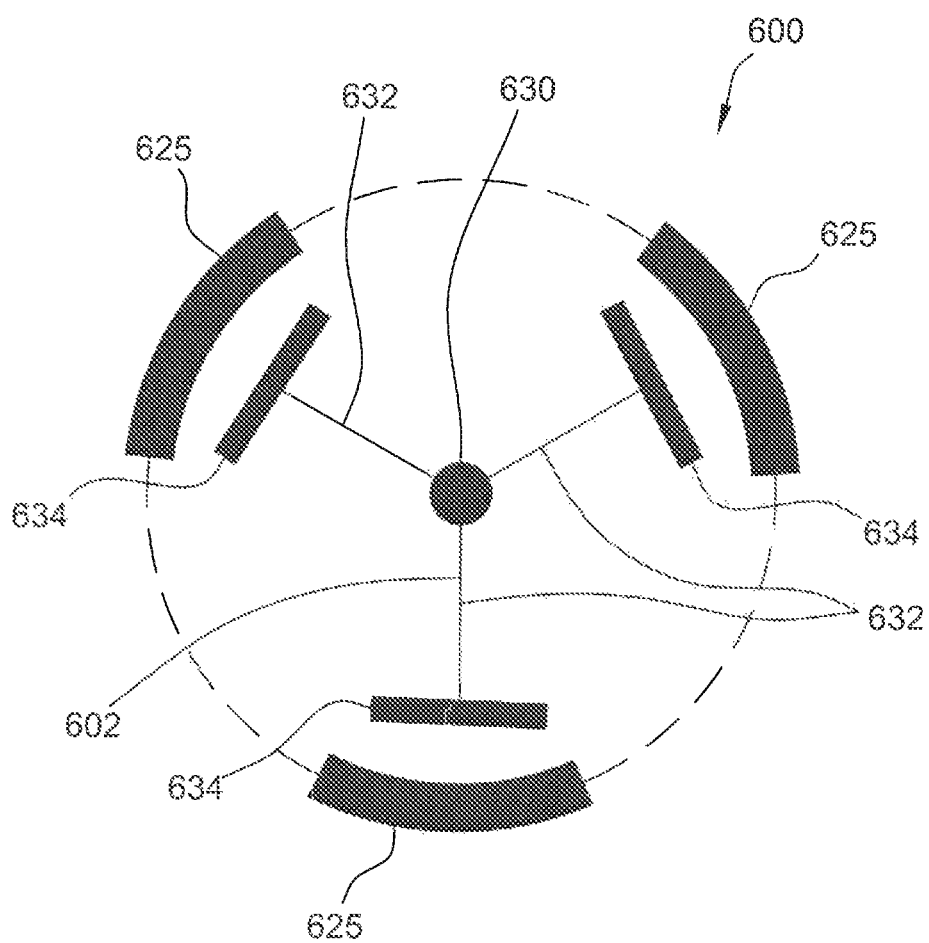
FIG. 7 is a cross-sectional schematic view of the DBS lead shown in FIG. 6 and a coupling component.

For example, FIG. 6 is a schematic view of a portion of a deep brain stimulation (DBS) lead 600, and FIG. 7 is a cross-sectional schematic view of DBS lead 600 and a coupling component 602 that may be used with DBS lead 600.

DBS lead 600 includes a plurality of electrodes 621. Specifically, DBS lead 600 includes several segmented electrodes 625. The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another.

As shown in FIG. 7, in this embodiment, coupling component 602 is positioned within DBS lead 600. Specifically, coupling component 602 includes a center 630 and three conductive branches 632 extending radially outward from center 630. Each conductive branch 632 terminates in a conductive plate 634 that is oriented generally parallel to a respective segmented electrode 625. Each conductive plate 634 effectively forms a capacitor with the respective segmented electrode 625.

Similar to ring coupler 306 and ring electrode 304, coupling component 602 is electrically isolated from segmented electrodes 625 at therapeutic frequencies. However, at MRI frequencies, coupling component 602 is electrically coupled to segmented electrodes 625. Accordingly, at MRI frequencies, segmented electrodes 625 are electrically coupled to one another, and collectively provide a larger surface area for dissipating RF energy and reducing heating. In some embodiments, a dielectric layer (not shown) is positioned between conductive plates 634 and associated segmented electrodes 625.

Figure 8:
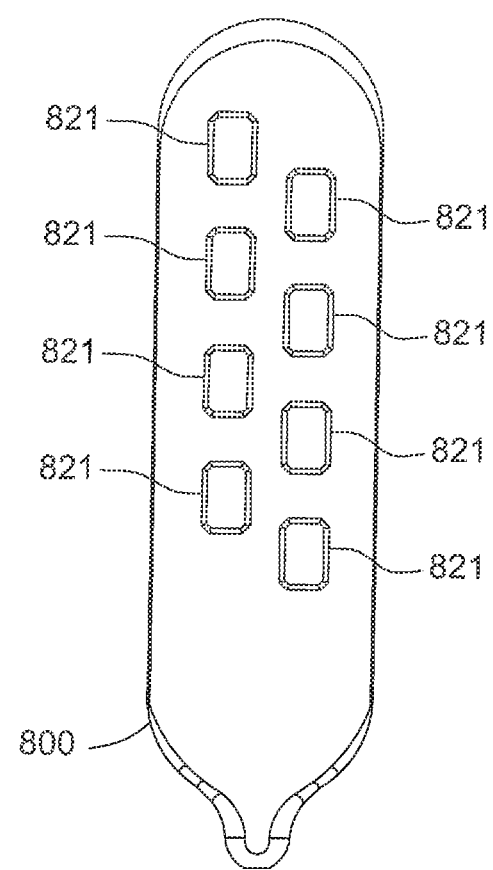
FIG. 8 is a schematic view of a portion of one embodiment of a spinal cord stimulation (SCS) lead.

As another example, FIG. 8 is a schematic view of a spinal cord stimulation (SCS) lead 800, and FIG. 9 is a cross-sectional schematic view of SCS lead 800 and a coupling component 802 that may be used with SCS lead 800.

SCS lead 800 includes a plurality of electrodes 821 arranged in a grid-like pattern. As shown in FIG. 9, in this embodiment, coupling component 802 is positioned within SCS lead 800. Specifically, coupling component 802 includes a conductive base 830 and conductive branches 832 extending from conductive base 830 towards electrodes 821. Each conductive branch 832 terminates in a conductive plate 834 that is oriented generally parallel to a respective electrode 821. Each conductive plate 834 effectively forms a capacitor with the respective electrode 821.

Similar to ring coupler 306 and ring electrode 304, coupling component 802 is electrically isolated from electrodes 821 at therapeutic frequencies. However, at MRI frequencies, coupling component 802 is electrically coupled to electrodes 821. Accordingly, at MRI frequencies, electrodes 821 are electrically coupled to one another and to conductive base 830, and collectively provide a larger surface area for dissipating RF energy and reducing heating. In some embodiments, a dielectric layer (not shown) is positioned between conductive plates 834 and associated electrodes 821.

Accordingly, the systems and methods described herein facilitate reducing RF heating of an implantable lead body during MRI therapy. Specifically, the systems and methods described herein reduce heating by having a relatively large electrode surface at MRI frequencies while having a smaller electrode surface during pacing or stimulation therapy. The heating reduction is achieved by electrically coupling a first electrode (e.g., a tip electrode) and a second electrode (e.g., a ring electrode) at MRI frequencies using a coupling component such that power deposited on the first electrode is distributed to the second electrode. The combination of the first and second electrodes has a larger surface area than the first electrode alone. Further, at pacing or stimulation frequencies, the first and second electrodes are electrically decoupled from one another.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:
1. An implantable lead comprising:
   a first electrode configured to deliver a first stimulation;

a second electrode configured to delivery a second stimulation; and a coupling component spaced from the first electrode,
wherein the first electrode and the coupling component form a capacitor, wherein the first electrode is electrically isolated from the coupling component and the second electrode at therapy frequencies, and wherein the first electrode is electrically coupled to the coupling component and the second electrode at magnetic resonance imaging (MRI) frequencies, wherein the first electrode is a ring electrode, and wherein the coupling component is a ring coupler that surrounds at least a portion of the ring electrode.

2. The implantable lead of claim 1, further a conductor extending along the lead to deliver stimulation therapy to the second electrode that is electrically coupled and physically coupled to the coupling component, wherein, when power is deposited on the first electrode at the MRI frequencies, the coupling component is configured to distribute the power to the second electrode.

3. The implantable lead of claim 1, wherein the implantable lead is a lead of a cardiac stimulation device, wherein the second electrode is a helical tip electrode, the ring and helical tip electrodes configured to delivery stimulation therapy and be electrically isolated from one another at therapy frequencies.

4. The implantable lead of claim 1, further comprising a flexible mechanism that electrically and physically couples the coupling component to the second electrode to allow relative movement between the coupling component and the second electrode.

5. The implantable lead of claim 1, further comprising a dielectric layer positioned between the first electrode and the coupling component.

6. An implantable lead comprising:
a first electrode configured to deliver a first stimulation;
a second electrode configured to delivery a second stimulation; and
a coupling component spaced from the first electrode,
wherein the first electrode and the coupling component form a capacitor, wherein the first electrode is electrically isolated from the coupling component and the second electrode at therapy frequencies, and wherein the first electrode is electrically coupled to the coupling component and the second electrode at magnetic resonance imaging (MRI) frequencies, wherein the implantable lead is a deep brain stimulation (DBS) lead, wherein the first electrode comprises a first segmented electrode, and wherein the second electrode comprises a second segmented electrode, wherein the coupling component comprises a plurality of conductive branches extending from a center of the DBS lead, wherein each conductive branch of the plurality of conductive branches terminates in a corresponding one of a plurality of conductive plates, and wherein the plurality of conductive plates comprise a first conductive plate oriented generally parallel to the first segmented electrode and a second conductive plate oriented generally parallel to the second segmented electrode.

7. An implantable lead comprising:
a first electrode configured to deliver a first stimulation;
a second electrode configured to delivery a second stimulation; and
a coupling component spaced from the first electrode, wherein the first electrode and the coupling component form a capacitor, wherein the first electrode is electrically isolated from the coupling component and the second electrode at therapy frequencies, and wherein the first electrode is electrically coupled to the coupling component and the second electrode at magnetic resonance imaging (MRI) frequencies, wherein the implantable lead is a spinal cord stimulation (SCS) lead, wherein the coupling component comprises a conductive base and a plurality of conductive branches extending from the conductive base, wherein each conductive branch of the plurality of conductive branches terminates in a conductive plate, and wherein the plurality of conductive plates comprise a first conductive plate oriented generally parallel to the first electrode and a second conductive plate oriented generally parallel to the second electrode.

8. An implantable medical device comprising:
an implantable pulse generator (IPG); and
an implantable lead coupled to the IPG, the implantable lead comprising first and second electrodes configured to deliver first and second stimulations, respectively, the implantable lead further comprising a coupling component spaced from the first electrode, wherein the first electrode and the coupling component form a capacitor, wherein the first electrode is electrically isolated from the coupling component and the second electrode at therapy frequencies, and wherein the first electrode is electrically coupled to the coupling component and the second electrode at magnetic resonance imaging (MRI) frequencies, wherein the first electrode is a ring electrode, and wherein the coupling component is a ring coupler that surrounds at least a portion of the ring electrode.

9. The implantable medical device of claim 8, wherein the second electrode is electrically coupled and physically coupled to the coupling component, wherein, when power is deposited on the first electrode at the MRI frequencies, the coupling component is configured to distribute the power to the second electrode.

10. The implantable medical device of claim 8, wherein the first electrode is a ring electrode, and wherein the second electrode is a helical tip electrode, the ring and helical tip electrodes configured to delivery stimulation therapy and be electrically isolated from one another at therapy frequencies.

11. The implantable medical device of claim 8, wherein the implantable lead further comprises a dielectric layer positioned between the first electrode and the coupling component to allow relative movement between the coupling component and the first electrode.

12. An implantable medical device comprising:
an implantable pulse generator (IPG); and
an implantable lead coupled to the IPG, the implantable lead comprising first and second electrodes configured to deliver first and second stimulations, respectively, the implantable lead further comprising a coupling component spaced from the first electrode, wherein the first electrode and the coupling component form a capacitor,
wherein the first electrode is electrically isolated from the coupling component and the second electrode at therapy frequencies, and wherein the first electrode is electrically coupled to the coupling component and the second electrode at magnetic resonance imaging (MRI) frequencies, wherein the implantable lead is a deep brain stimulation (DBS) lead, wherein the first electrode comprises a first segmented electrode, and wherein the second electrode comprises a second segmented electrode, wherein the coupling component comprises a plurality of conductive branches extending from a center of the DBS lead, wherein each conductive branch of the plurality of conductive branches terminates in a corresponding one of a plurality of conductive plates, and wherein the plurality of conductive plates comprise a first conductive plate oriented generally parallel to the first segmented electrode and a second conductive plate oriented generally parallel to the second segmented electrode.

13. The implantable medical device of claim 8, wherein the implantable lead is a spinal cord stimulation (SCS) lead.

14. An implantable medical device comprising:
an implantable pulse generator (IPG); and
an implantable lead coupled to the IPG, the implantable lead comprising first and second electrodes configured to deliver first and second stimulations, respectively, the implantable lead further comprising a coupling component spaced from the first electrode, wherein the first electrode and the coupling component form a capacitor, wherein the first electrode is electrically isolated from the coupling component and the second electrode at therapy frequencies, and wherein the first electrode is electrically coupled to the coupling component and the second electrode at magnetic resonance imaging (MRI) frequencies,
wherein the implantable lead is a spinal cord stimulation (SCS) lead,
wherein the coupling component comprises a conductive base and a plurality of conductive branches extending from the conductive base, wherein each conductive branch of the plurality of conductive branches terminates in a conductive plate, and wherein the plurality of conductive plates comprise a first conductive plate oriented generally parallel to the first electrode and a second conductive plate oriented generally parallel to the second electrode.

\* \* \* \* \*